United States Patent [19]
Anderson

[11] Patent Number: 5,464,285
[45] Date of Patent: Nov. 7, 1995

[54] BAG WITH PERFORATED OPENING

[75] Inventor: Richard F. Anderson, Overland Park, Kans.

[73] Assignee: Venture Packaging, Inc., Charlotte, N.C.

[21] Appl. No.: 241,598

[22] Filed: May 12, 1994

[51] Int. Cl.⁶ .................................................. B65D 33/08
[52] U.S. Cl. ................................. 383/10; 383/66; 383/207
[58] Field of Search ............................... 383/9, 10, 207, 383/66

[56] References Cited

U.S. PATENT DOCUMENTS

| | | |
|---|---|---|
| 2,306,335 | 12/1942 | Feigenbutz ............................... 383/207 |
| 3,227,359 | 1/1966 | Hanlon ..................................... 383/207 |
| 3,520,470 | 7/1970 | Korn et al. . | 
| 3,730,421 | 5/1973 | Stanley . |
| 3,873,735 | 3/1975 | Chalin et al. . |
| 4,252,269 | 2/1981 | Peppiatt . |
| 4,539,705 | 9/1985 | Baines . |
| 4,573,203 | 4/1989 | Peppiatt . |
| 4,934,535 | 6/1990 | Muckenfuhs et al. . |
| 4,966,286 | 10/1990 | Muckenfuhs . |
| 5,036,978 | 8/1991 | Frank et al. . |
| 5,219,229 | 6/1993 | Sengerwald .............................. 383/10 |
| 5,282,687 | 2/1994 | Yee ........................................ 383/207 |

*Primary Examiner*—Stephen P. Garbe
*Attorney, Agent, or Firm*—Shefte, Pinckney & Sawyer

[57] ABSTRACT

A plastic bag for containing merchandise which includes a plurality of walls forming a compartment for receiving and containing the merchandise, a generally flat flap connected at the top wall of the bag so as to be capable of extending outwardly therefrom, and perforations formed in the flap and in the container walls in a particular pattern that permits the perforations in the flap to be separated to form a handle opening in such flap without opening the bag itself, and which can be further opened to provide an access opening in the bag to permit removal of the merchandise therefrom.

6 Claims, 4 Drawing Sheets

BAG WITH PERFORATED OPENING

BACKGROUND OF THE INVENTION

The present invention relates generally to bags for receiving and containing merchandise, and more particularly to plastic bags that are provided with a handle to allow customers to carry the bag more easily.

It is now common practice to manufacture bags from a thin transparent material, such as polyethylene or a similar heat-sensitive plastic, and to supply such bags to producers of a wide variety of consumer merchandise (e.g., diapers) who then load the bags with such merchandise and provide the filled bags to retail outlets for sale to consumers. These filled bags are frequently stacked together, such as along aisles located in the retail outlet, where they can be seen by consumers, and when the consumer decides to buy the product, the bag is lifted from the stack and carried away. When the merchandise contained in the bag is heavy and/or bulky, the bags are preferably made with some type of handle that will assist the consumer in carrying the bag.

Plastic bags with handles take a variety of forms and one such bag is disclosed in Baines U.S. Pat. No. 4,539,705 and includes a handle that is formed as a separate piece of plastic which is initially disposed within the gusset of the bag and sealed to the walls of the bag to provide a bag that is capable of withstanding heavy loads while at the same time presenting a neat appearance.

Another typical plastic bag with a handle is disclosed in Peppiatt U.S. Pat. No. 4,252,269, and this bag includes a handle that is either formed from the same piece of plastic material as the bag shell, or from a separate piece of material that is heat sealed at the top wall of the bag. In either case, the handle piece is a relatively large flap that projects outwardly from the top wall of the bag and this flap is formed with an opening through which the consumer inserts his or her hand when carrying the bag. This type of handle bag has the advantage of permitting the handle to serve as a "billboard" in that advertising and informational text and illustrations can be presented on the handle so as to catch the eye of and, hopefully, attract passing consumers. However, the aesthetic appeal of such billboard handles, and the continuity of the textural material and illustrations presented thereon, are adversely affected by the relatively large hand-receiving opening that is located in the middle of the handle flap.

Plastic bags of this general type may also be provided with some arrangement to assist the consumer in opening the bag to remove the contents therefrom. In most cases, the plastic bags are filled with merchandise and then completely sealed by the manufacturer to protect such merchandise, and the consumer often encounters some difficulty in penetrating the bags to remove its contents. There are a number of known bags which include some type of construction to facilitate opening the bag, such as a perforation extending along the top surface of the gusset of the bag as disclosed in Peppiatt U.S. Pat. No. 4,573,203, or a combination of tabs and perforations that allow the consumer to grasp the tab and pull away a portion of the bag as disclosed, for example, in Muchenfuhs U.S. Pat. No. 4,966,286 and 4,934,535 and Chalin U.S. Pat. No. 3,873,735. It is also known to provide plastic bags with perforations that permit the handle portion of the bag to partially separate from the bag so that the handle can be more easily grasped, as disclosed, for example, in Stanley U.S. Pat. No. 3,730,421 and Korn U.S. Pat. No. 3,520,470.

SUMMARY OF THE INVENTION

In accordance with the present invention, a bag is formed of a thin, flaccid material to contain merchandise and the like, and the bag includes a plurality of walls which form a compartment for receiving and containing such merchandise, a generally flat handle flap connected at one of its edges to the exterior of one of the walls so as to be capable of extending outwardly therefrom, and a line of weakness, preferably in the form perforations, formed in the flap and in the wall to which the flap is attached to permit the bag material to be selectively open along the line of weakness. The line of weakness is disposed in a pattern that includes a first portion forming a handle opening in the flap of a predetermined size large enough to receive a human hand when the plastic material is separated along the first portion of the pattern and a second portion forming an access opening in the container wall to which the flap is attached, such opening being of a predetermined size large enough to permit removal of the merchandise through the access opening when the bag material is separated along the second portion of the pattern.

In the preferred embodiment of the present invention, both the first and second portions of the line of weakness pattern are formed by perforations and the line of weakness includes a small unperforated bridge disposed intermediate the first and second portions of the pattern, such bridge being dimensioned to permit the material of the flap to be opened along the perforations of the first portion of the pattern by application of a first opening force applied at the first portion of the pattern without opening the perforations of the second portion of the pattern and to permit the wall to which the flap is attached to be selectively opened along the perforations of the second portion of the pattern by the application of a second opening force applied to the aforesaid unperforated bridge. Moreover, the first portion of the pattern is preferably generally T-shaped so as to include an elongated strip located generally centrally of the flap and to include a narrow leg extending between such strip and the edge of the flap that is attached to the adjacent wall, and the second portion of the pattern also includes a narrow leg that corresponds to the narrow leg of the T-shaped portion and is generally aligned therewith. The unperforated bridge is disposed between these aligned narrow legs.

DESCRIPTION OF THE PREFERRED EMBODIMENT

Figure 1:
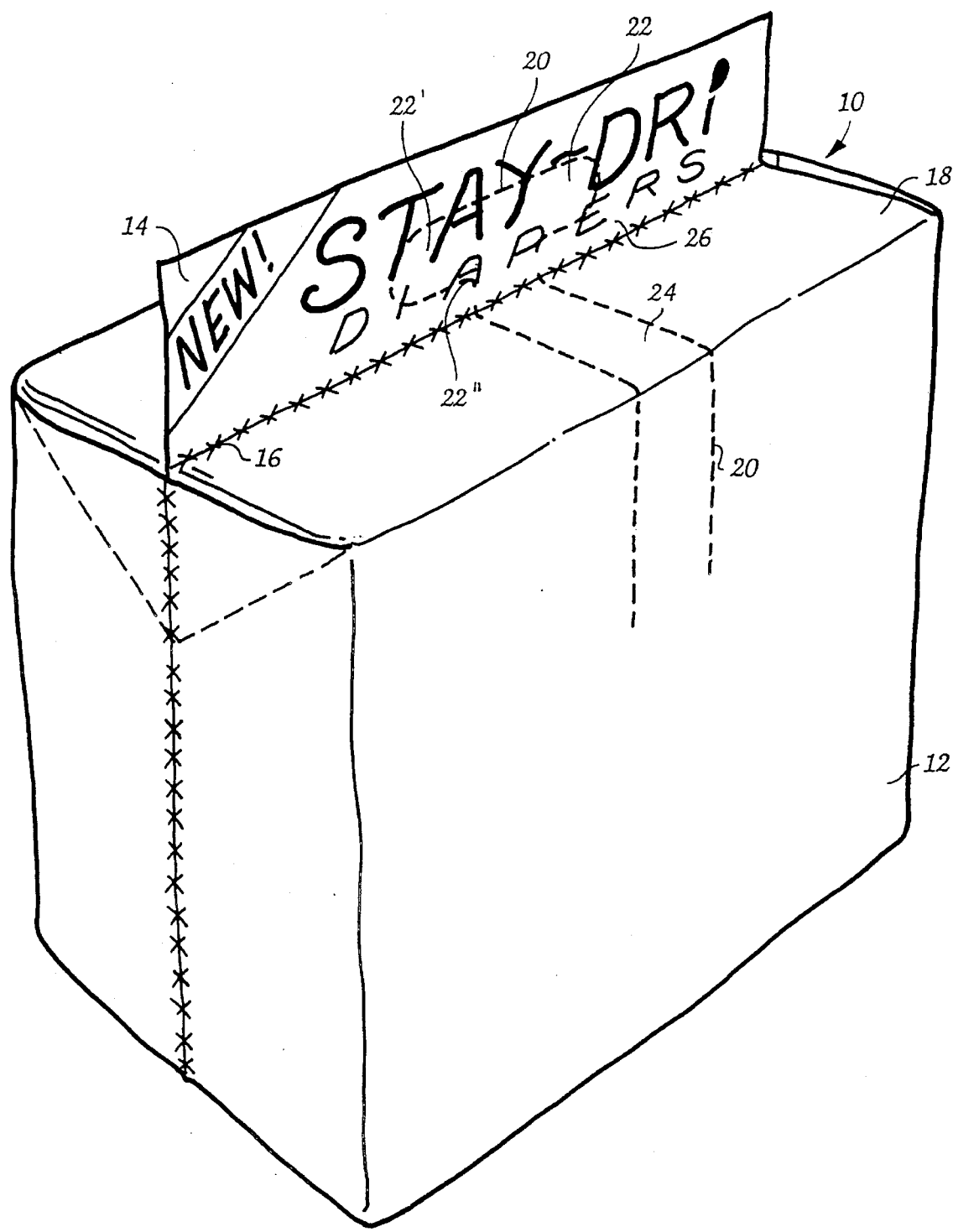
FIG. 1 is a perspective view of a plastic bag constructed in accordance with the preferred embodiment of the present invention.

Looking now in greater detail at the accompany drawings, the bag 10 of the present invention is preferably formed of a plastic material such as a thin sheet of polyethylene or a similar heat-sensitive plastic, and in the preferred embodiment the bag has a parallelepiped compartment 12 for receiving and containing merchandise therein, and a generally flat flap 14 that is heat sealed along line 16 at one of its edges along the extent of the gusset wall 18 of the container portion 12 so that the flap 14 is capable of extending outwardly therefrom as illustrated in FIG. 1 or lying flat against the gusset wall 18.

Figure 2:
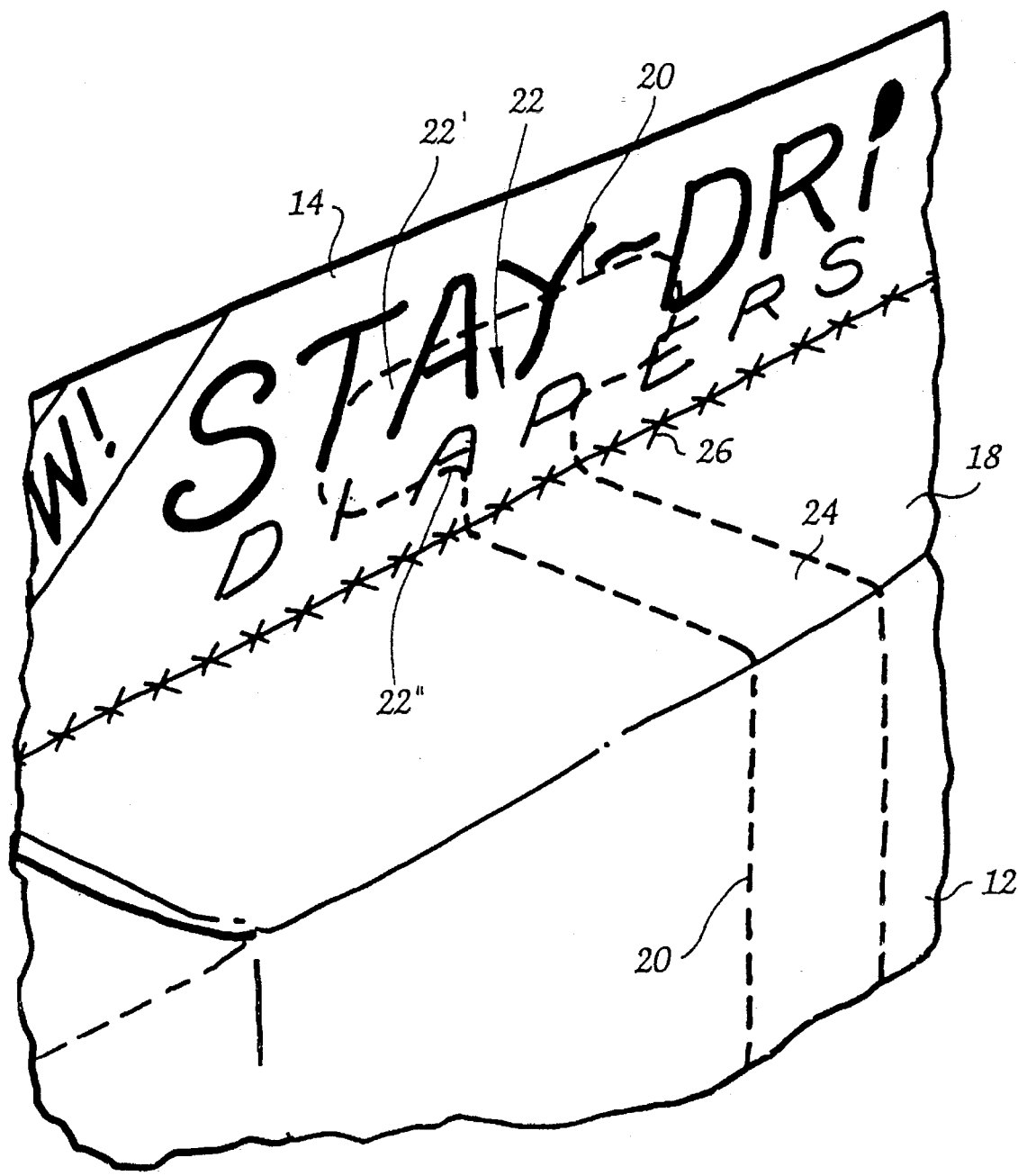
FIG. 2 is a detail view illustrating the pattern of perforations in the handle portion and the container portion of the bag illustrated in FIG. 1.

As best seen in FIG. 2, the flap 14 and the container portion 12 are formed with perforations 20 arranged in a particular pattern that includes a first T-shaped portion 22 formed in the flap 14, such T-shaped portion including an elongated shape 22' that is located generally centrally of the flap 14 and a narrow leg portion 22" extending toward the edge of the flap 14 that is attached to the gusset wall 18. The pattern of perforations 20 also includes a second portion 24 formed in the container 12 as a narrow leg extending along the gusset wall 18 and along one of the side walls of the container 12. The second narrow leg portion 24 is generally aligned with the narrow leg portion 22" in the flap 14, and both narrow leg portions have substantially the same width. However, as best seen in FIG. 2, there is a relatively small unperforated bridge 26 located adjacent the heat sealed line 16 and disposed between the adjacent ends of the flap leg portion 22" and the container narrow leg portion 24, this bridge 26 being dimensioned to permit the T-shaped portion 22 to be separated from the flap 14 by the application of a first opening force applied to the T-shaped portion without also opening the perforations of the second narrow leg portion 24 in the gusset wall 18, but permitting the second narrow leg portion 24 to be separated from the gusset wall 18 by the application of a second opening force applied at the bridge 26, all as explained in greater detail below.

It will be understood that the bags 10, as best seen in FIG. 1, are usually preprinted with illustrations and textural material, after which the bags are provided to the producer who then fills the bags with the product to be contained therein and the bottom of the bag is then sealed so that the interior of the container portion 12 is essentially free of contamination. The bags filled with merchandise are ultimately shipped to retail outlets, where they are usually displayed in a conventional manner to customers shopping at such retail outlets. It will be apparent that the textural material and illustrations which are preprinted on the bag serve a significant function in attracting the attention of consumers passing by the bags which are on display, and in providing brand identification and other information that may be useful to the consumer in deciding which product to buy.

The bag 10 of the present invention offers a new dimension to this "billboard" function of the bag by providing a flat, uninterrupted surface on which additional textural material and illustrations can be placed at a point where they are particularly visible to passing consumers. More specifically, the flap 14 of the bag 10 is located at the top wall 18 so that it is at a very visible location whether it is lying flat against the top wall 18 or projecting upwardly therefrom as best seen in FIG. 1. Also, because there is no handle opening in the flap 14, and because the perforations 20 are barely visible, the flap 14 provides a relatively large and uninterrupted surface on which a significant amount of textural material and illustrations can be attractively presented.

Figure 3:
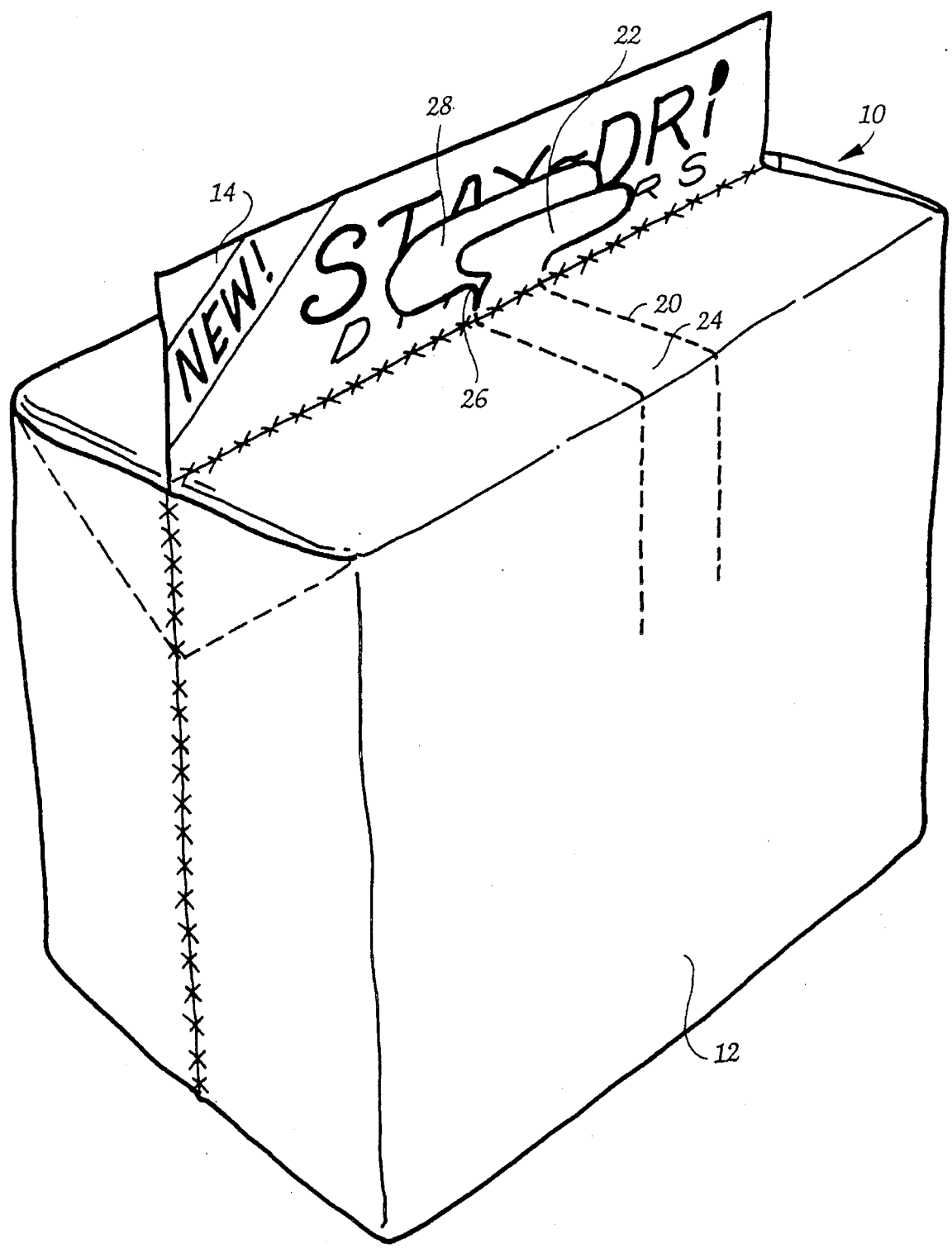
FIG. 3 is a perspective view of the bag illustrated in FIG. 1, illustrating the perforated portion of the bag being partially opened to create the handle opening in the flap of the bag.

Additionally, the flap 14 of the present invention also provides all of the advantages of a conventional handle for such bags. A consumer who has selected the product in one of the bags 10 of the present invention can quickly and easily form a handle opening 28 in the flap 14 by applying a first opening force at the T-shaped portion 22 of the pattern of perforations 20, whereby the T-shaped portion 22 separates from the flap 14 as illustrated in FIG. 3 to leave the handle opening 28 in the flap 14. Moreover, it will be noted that the bridge 26 is dimensioned so that the first pressure needed to separate the T-shaped portion 22 will not be sufficient to tear the material across the bridge 26 and, therefore, only the T-shaped portion 22 will be separated along the perforations 20. Accordingly, the integrity of the sealed container portion 12 is left intact, and the product remains fully contained therein without any danger of contamination.

Figure 4:
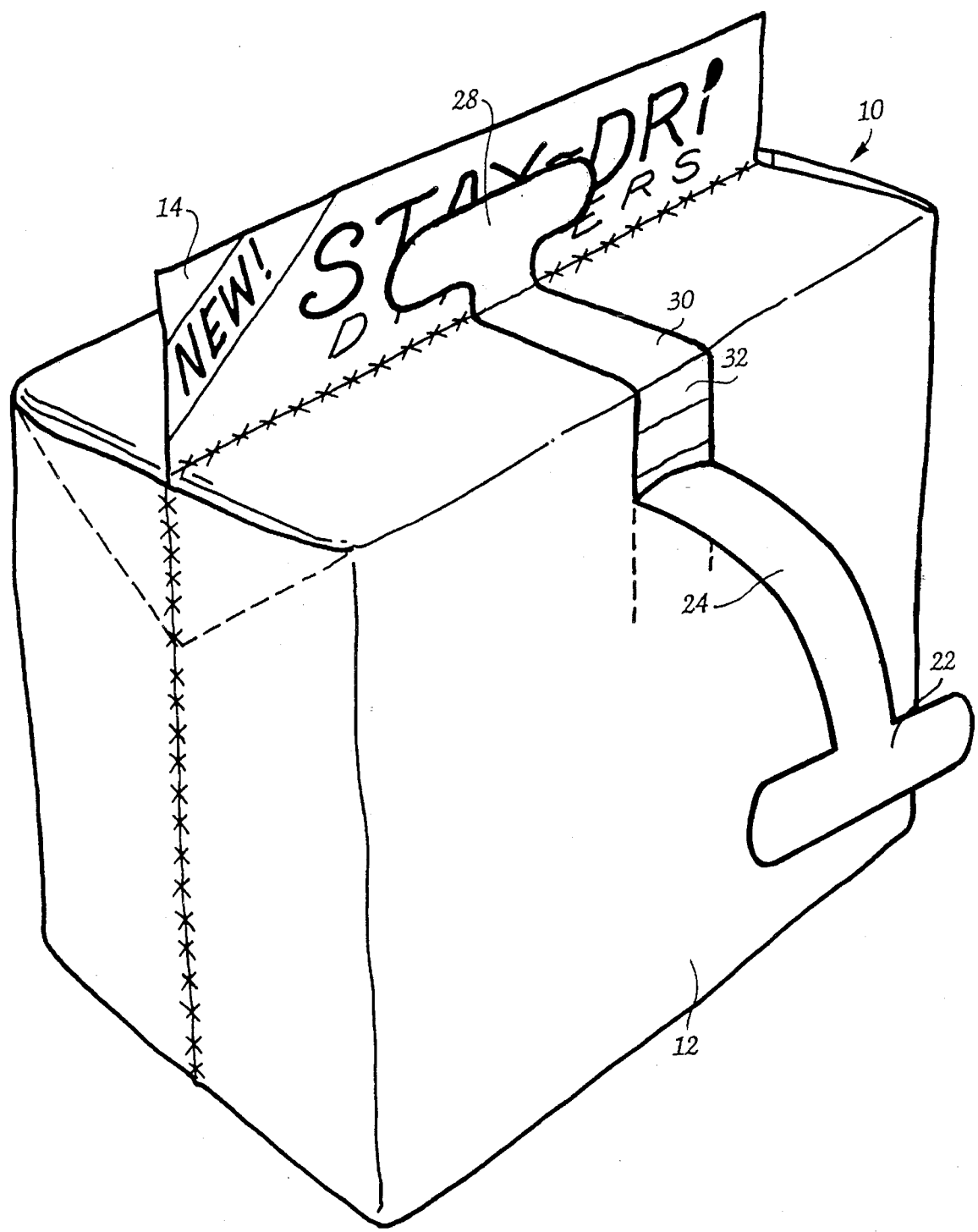
FIG. 4 is a perspective view similar to FIG. 3 and illustrating the perforated portion of the bag being substantially fully opened.

After the bag 10 has been carried to its destination, using the handle opening 28 to carry the bag 10, it can thereafter be easily opened to remove product therefrom by applying a second force in the form of a pull on the separated T-shaped portion 22, such pull being of a magnitude that will cause the bridge 26 between the aligned narrow portions 22" and 24 to tear, whereupon the second narrow leg portion 24 separates from the top wall and side wall of the container 12 along the perforations 20 therein as best illustrated in FIG. 4 to thereby provide an access opening through which the contained product 32 (e.g., diapers) can be easily removed.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A bag formed of a thin, flaccid material for containing merchandise and the like, said bag including:

(a) a plurality of walls forming a compartment for receiving and containing said merchandise;

(b) a generally flat flap connected at one of its edges to the exterior surface of one of said walls so as to be capable of extending outwardly therefrom; and (c) a line of weakness formed in said flap and in said one wall to permit said bag material to be selectively opened along said line of weakness, with said line of weakness being disposed in a pattern that includes a first portion forming a handle opening in said flap of a predetermined size large enough to receive at least a portion of a human hand when said bag material is separated along said first portion of said pattern, and a second portion forming an access opening in said one wall of a predetermined size large enough to permit removal of said merchandise through said access opening when said bag material is separated along said second portion of said pattern.

2. A bag as defined in claim 1 wherein said pattern of said line of weakness includes perforations in said flap forming said first portion thereof, and perforations in said one wall forming said second portion thereof, and includes a small unperforated bridge disposed intermediate said first and second portion of said pattern, said bridge being dimensioned to permit said material of said flap to be opened along the perforation of said first portion by the application of a first opening force applied at said first portion of said pattern without opening the perforation of said second portion, and to permit said wall to be selectively opened along the perforation of said second portion by the application of a second opening force applied at said bridge.

3. A bag as defined in claim 2 wherein said first portion of said pattern is generally T-shaped and includes an elongated strip located generally centrally of said flap and a narrow leg extending between said elongated strip and said edge of said flap that is attached to said one wall, wherein said second portion of said pattern includes a narrow leg corresponding to said narrow leg of said first pattern portion and generally aligned therewith, and wherein said bridge is disposed between said aligned narrow legs.

4. A bag as defined in claim 1 wherein said bag is formed of plastic material, wherein said one wall is a gusset, and wherein said one edge of said flap is heat sealed to said gusset.

5. A bag as defined in claim 1 wherein said first portion of said pattern is generally T-shaped and includes an elongated shape located generally centrally of said flap and a narrow leg extending between said elongated shape and said edge of said flap that is attached to said one wall, and in that second portion of said pattern includes a narrow leg corresponding to said narrow leg of said first pattern portion and generally aligned therewith.

6. A bag formed of plastic material for containing merchandise and the like, said bag including:

(a) a plurality of walls arranged as a right angle parallelepiped to form a compartment for receiving and containing said merchandise, with one of said walls being a gusset;

(b) a generally flat flap heat sealed at one of its edges along the extent of said gusset wall so as to be capable of extending outwardly therefrom; and (c) perforations formed in said bag to permit opening said bag therealong and disposed in a pattern that includes:

(i) a first generally T-shaped portion forming an elongated shape positioned generally centrally within said flap and dimensioned to receive a human hand when opened along said perforation, and forming a narrow leg extending from said elongated shape and toward said heat seal between said flap and said gusset;

(ii) a second portion forming a narrow leg extending along said gusset and generally aligned with said narrow leg of said first pattern portion for providing an access opening through which said merchandise can be removed from said bag when the perforated second pattern portion is opened; and (iii) a small unperforated bridge disposed between said aligned narrow legs of said first and second pattern portion, and at said heat seal, said bridge being dimensioned to permit said plastic bag to be opened along the perforation of said first pattern portion by the application of a first force applied at said first portion without opening the perforation of said second pattern portion, and to permit said gusset wall to be selectively opened along the perforation of said second pattern portion by the application of a second opening force applied at said bridge.

* * * * *